United States Patent [19]

Chin et al.

[11] Patent Number: 4,493,711

[45] Date of Patent: Jan. 15, 1985

[54] TUBULAR EXTRUSION CATHETER

[75] Inventors: Albert K. Chin, San Francisco, Calif.; Thomas J. Fogarty, 770 Welch Rd., Palo Alto, Calif. 94304

[73] Assignee: Thomas J. Fogarty, Palo Alto, Calif.

[21] Appl. No.: 392,279

[22] Filed: Jun. 25, 1982

[51] Int. Cl.³ .............................................. A61M 25/00
[52] U.S. Cl. ..................................... 604/271; 128/344; 128/348.1
[58] Field of Search ...................... 128/325, 344, 348.1; 604/93, 271

[56] References Cited

U.S. PATENT DOCUMENTS

| | | | |
|---|---|---|---|
| 3,168,092 | 2/1965 | Silverman | 604/96 X |
| 4,043,345 | 8/1977 | Kramann et al. | 604/271 |
| 4,109,659 | 8/1978 | Sheridan | 604/271 |
| 4,271,839 | 6/1981 | Fogarty et al. | 604/271 |

Primary Examiner—Dalton L. Truluck
Attorney, Agent, or Firm—Limbach, Limbach & Sutton

[57] ABSTRACT

A catheter of the evagination type is provided with an inverted-evertable non-elastic tube having a diameter throughout equal to or greater than the catheter body, an axially aligned end opening at the distal end, and a multifold configuration of the distal end to maintain end-sealing during inversion and eversion.

5 Claims, 7 Drawing Figures

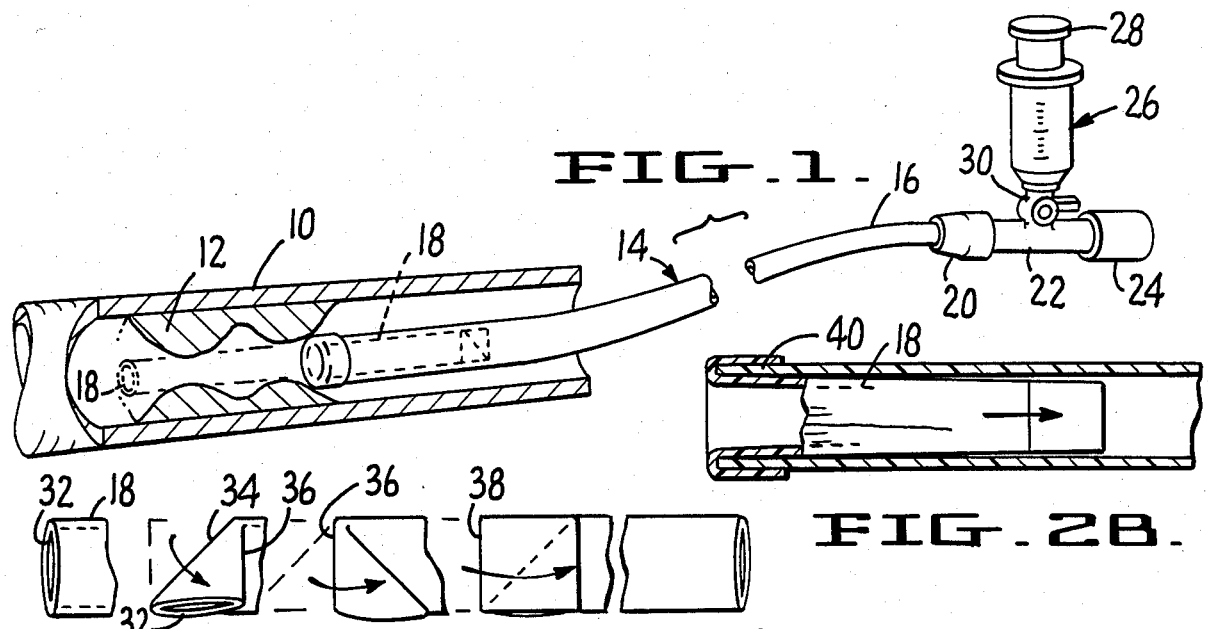
FIG.1.
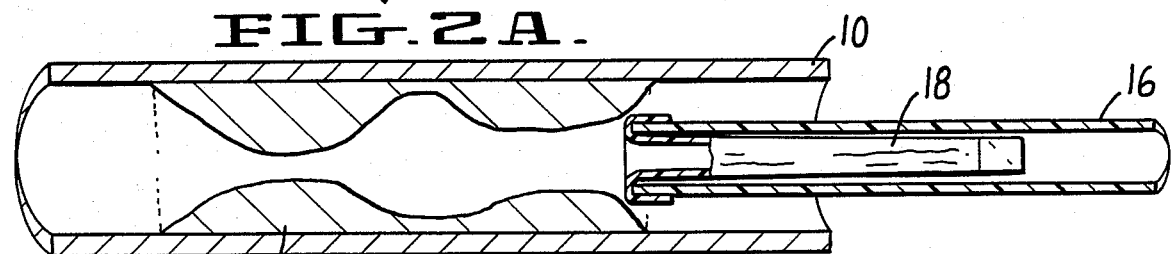
FIG.2B.
FIG.2A.
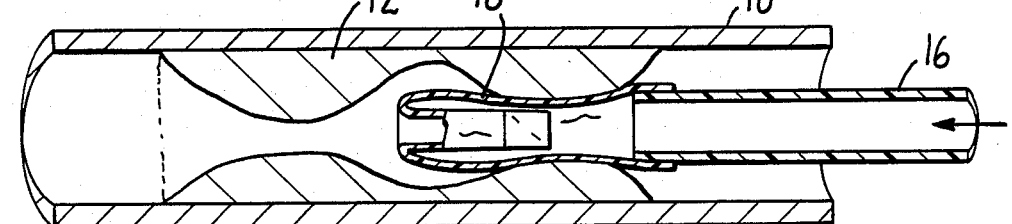
FIG.3.
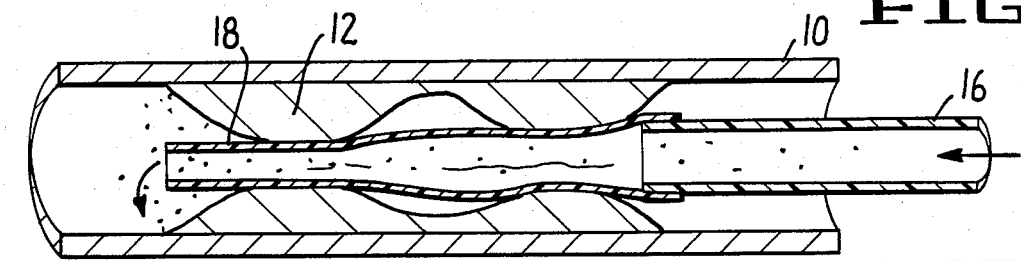
FIG.4.
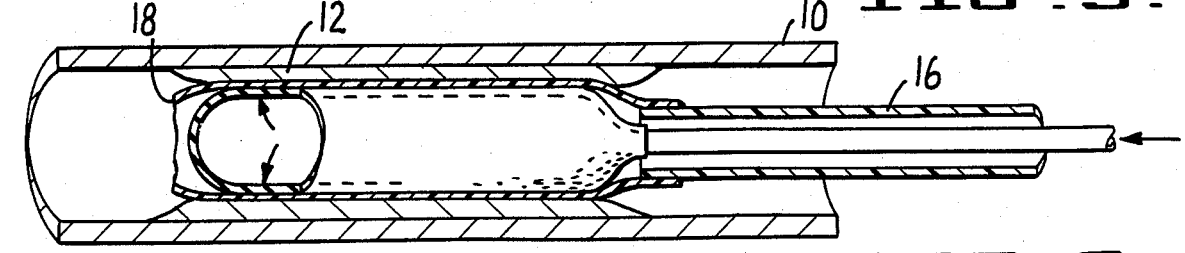
FIG.5.
FIG.6.

TUBULAR EXTRUSION CATHETER

BACKGROUND OF THE INVENTION

The invention pertains to a catheter which is provided with a tube which is carried in an inverted position within the catheter and everted from the catheter during use.

Reference may be had to U.S. Pat. No. 4,109,659 as the most significant prior art of which we are aware as to the subject invention. The subject catheter differs from the one shown in that patent in several important regards which adapt the present catheter to a number of uses for which this prior art evagination catheter is not suitable. The principal differences between our catheter and this prior art catheter are: our tube is non-elastomeric; it has an inner diameter equal to or greater than the diameter of the catheter body; and the distal tip of the tube is folded in a manner to close off the previously open distal end of the tube and to maintain this distal end in closed condition until the full length of the tube has been everted from the catheter body. In the final phase of the tube eversion process, the folded tip flips to an inside-out condition, thus conditioning the tube end to unfolding to present a through lumen to the overall tubular extrusion catheter.

SUMMARY OF THE INVENTION

A principal object of the tubular extrusion catheter of the invention is the provision of a means for placement of soft, non-elastomeric tube through the lumen of a normal or occluded artery, vein, or other body passageway, such as the intestine. The catheter may be used for various purposes. It may be used for the injection of therapeutic or diagnostic agents into the body passageway. It may be used as a guide for the passage of another instrument, such as visual apparatus, a biopsy tool, or a dilatation catheter, into the body passageway. It may be used to recanalize a complete thrombus prior to the injection into the occlusion zone of a fibrinolytic material. It may be used for body cavity or passageway drainage purposes and also to provide an indwelling venous line for physiological measurements and delivery of drugs.

BRIEF DESCRIPTION OF THE DRAWING

FIG. 1 is a view in perspective of the subject catheter in associated relation to an occluded artery;

FIG. 2A is a view of the tube before attachment to the catheter body, showing the preferred manner and sequence of folding of the open end of the tube;

FIG. 2B is a view partly in section and partly in elevation of the catheter body with tube attached and inverted within the body;

FIG. 3 shows a view in diametral section of an occluded artery showing the initial stage of emplacement of the subject catheter therein;

FIG. 4 is a view like that of FIG. 3 but showing the tube in partially everted condition;

FIG. 5 is also a view like that of FIG. 3 showing the catheter tube in fully everted condition and showing the catheter in use for the injection into the occlusion zone of treatment material;

FIG. 6 is a view like that of FIG. 3 showing the subject catheter in tube-everted condition being used to accommodate a dilatation catheter.

DESCRIPTION OF THE PREFERRED EMBODIMENT

FIG. 1 shows an artery 10 containing occlusion 12. The catheter 14 shown in associated relation therewith comprises a flexible plastic tube 16 and an evertable tube 18 attached to the distal end of tube 16. The tube 16 is fixedly attached to an internally threaded coupling member 20 which is attached to the externally threaded end of a T-shaped fitting 22. The proximal end of fitting 22 is attached to a terminal member 24 which may be provided at its proximal end with a removable closure plug.

A syringe 26 is connected to the proximal end of the catheter 14 through the fitting 22. The syringe is to be filled with an incompressible fluid. Syringe plunger 28 and control valve 30 constitute means whereby the fluid may be selectively charged into the catheter.

Prior to attachment of the tube 18 to the catheter body 16, the open distal end 32 is closed as illustrated in FIG. 2A. First, the distal end portion of tube 18 is folded about biasfold line 34. Then, the distal end portion of tube 18 is folded about a transverse fold line such as 36. The distal end portion is then folded once again about a transverse fold line such as 38.

The folded end portion of tube 18 is then inserted into tube 16, as shown in FIG. 2B. The proximal end 40 of tube 18 is then folded over the distal end of tube 16 and adhesively attached thereto.

A typical initial positioning of the catheter with inverted tube is shown in FIG. 3. In this position, pressurized fluid is admitted into the catheter to evert the tube through the occlusion zone, as shown sequentially in FIGS. 4–5, with a minimum of relative movement between the interengaging surfaces of the everting tube and occlusion 12. The pressurized fluid maintains the folded end of the tube in closed and sealed condition until such time as the folded end turns inside-out as it everts from the balance of the tube. The fluid then causes the end of the tube to unfold and open.

FIG. 4 shows the open tube being used as a conduit for injection into the occlusion zone of treatment material.

FIG. 5 shows the catheter being used as a guide for a dilatation catheter 42.

One of the major proposed uses of our tubular extrusion catheter is the use of it to provide a passageway for the introduction of another device such as an inverted balloon dilatation catheter. In this capacity, the tubular extrusion catheter unrolls its way to a position proximal to the main stenosis that is to be dilated by the dilatation catheter or it may actually unroll its way through the stenosed segment. The tubular extrusion catheter has the capability of partially dilating stenoses which exists throughout its pathway. After the tubular extrusion catheter has been unrolled, the dilatation catheter is advanced within the lumen of the unrolled tube to dilate the stenosis. In order to properly accomplish this described sequence, the subject catheter must differ in several important respects from the evagination catheter shown in U.S. Pat. No. 4,109,659.

In the first place, in order to allow the introduction of another device, such as a dilatation catheter, past the distal end of the fully extruded tube, the tube must be open at its own distal end rather than along the side of its distal end, as in the cited prior art patent. This requirement in turn requires the above-described folded tip configuration rather than, as in the cited prior art patent, tip inversion and insertion into the tube. A side opening is satisfactory for drainage and medication infusion purposes but not for the introduction of other devices such as catheters into, and sometimes through, the tube of the subject tubular extrusion catheter.

The fully everted tube of the subject catheter must allow a dilatation catheter to pass through the tube and, in some cases, it must allow the dilatation catheter balloon to inflate and dilate a stenosis from within the lumen of the extended tube. The diameter of the entire extended tube must therefore be from one to two times the outer diameter of the catheter body 16 or greater. The catheter of the cited patent has a tapered tube with a maximum diameter corresponding to that of the catheter body. The tapered tube will not allow passage of a dilatation catheter or permit dilatation to be practiced from within the lumen of the tube, as with the subject catheter.

The concept of using a tube of larger diameter than the catheter body in turn requires different concepts as to the material to be used for construction of the tube and as to the method and means for closing the distal end of the tube.

The material used for the tube of the subject catheter must be relatively non-elastomeric in order not to overdistend when it meets resistance during extrusion, as when it acts to partially dilate a stenosis. The material must also be pliable to allow the folding of the distal tip of the tube a number of times, as above described. A material having these desired characteristics is polyethylene, a preferred material for the tube. The material from the tube of the catheter of the cited patent is required to be able to maintain its shape well enough to form a seal or stopper to avoid leakage during evagination. This requires that the material be an elastomeric type having a spring-like consistency, characteristics which would cause the material to resist the tip-folding procedure followed in connection with the subject catheter. The use of such a material for the tube of the subject catheter would make our catheter unsuitable for dilatation application.

The use in the subject catheter of a large diameter tube which must fit into a smaller diameter catheter body requires that the tube, including the folded tip, be bent or folded along its longitudinal axis. Such a longitudinal fold will not disturb the multi-fold end sealing of the tube during the evagination process, but in the catheter of the patent even a partial fold along the longitudinal axis of the tube could effect a relative movement between the inverted tip and the tube and thereby disturb the sealing of the tube against leakage.

As long as the folded distal tip of the catheter remains folded, the tube 18 has the capability of maintaining its internal pressure condition and of rolling through stenoses and tortuous passages with less shear force than results from manual advancement of conventional catheters. The necessity for the folded distal tip of the tube to flip to an inside-out condition prior to unfolding results in the pressure holding property of the tube during the eversion of substantially the entire length of the tube. The fact that the tube holds pressure and does not leak during the eversion process means that substantially the entire length of the tube may be rollingly extruded from the catheter. Such unrolling action makes the passage of the tube through body passageways less traumatic than is the case with most other catheters. The unrolling action of the extruding tube makes vessel or intestinal perforation unlikely during advancement of the tube to the desired position.

The present catheter allows the establishment of a lumen through a completely occluding thrombus prior to injection of fibrinolytic agents. Thus, these agents will be considerably more effective in further recanalization of a lumen. Present methods inject fibrinolytic material proximal to the thrombus only, and recanalization of the vessel may not be established in every case. This is likely, for example, where there is a lengthened clot or propagated thrombus. The combined fibrinolytic injection plus mechanical action of the tubular extrusion catheter in rollingly boring its way through a completely occluding thrombus increases the therapeutic efficiency of the procedure in all instances.

Presently known venous catheters, for example those used in the external jugular or subclavian veins, are not completely flexible and invariably make several points of contact with the vessel wall while they are positioned in the vein. These catheters may be left in place for weeks, and the shearing action of these catheters against the points of the vessel wall being contacted tend to strip the endothelial surface of the vessel, forming nidi for thrombosis. The present catheter uses a softer tube which conforms to the vessel's shape. The tube does not tend to rub repeatedly against the same spot in the vessel wall, but makes gentler contact, thus decreasing the complications from use of an indwelling line. The incidence of trauma during the initial placement of the venous line is also reduced inasmuch as the tube unrolls into position rather than being advanced with rubbing action against the vessel wall.

What is claimed is:

1. A catheter comprising an elongated flexible tubular catheter body, a non-elastomeric flexible tube of a generally uniform diameter over the entire length thereof at least one to two times that of the outer diameter of the catheter body, said tube having first and second initially open ends, the first end being closed by being folded externally several times upon itself and then turned outside-in so as to be secured within the tube, and then being inserted into said body, the second end being turned inside-out and being sleeved over and secured to the distal end of said body, said folded and closed first end being adapted to remain folded and closed upon the application of pressurized fluid thereto through the catheter body to cause the eversion of said tube from said body and said folded and closed end being adapted at the end of eversion movement of said tube to flip to an inside-out condition and open under continued application of pressurized fluid.

2. The catheter of claim 1 wherein the tube is formed of polyethylene.

3. The catheter of claim 1, the diametral dimension of said tube being about 1–2 times as great as the internal diametral dimension of said body.

4. A catheter comprising an elongated flexible tubular catheter body, a flexible tube having first and second initially open ends, the first end being closed by being folded several times upon itself through a biasing fold to dispose said end normal to the longitudinal axis of said tube and a plurality of successive lapping folds taken at right angles to said longitudinal axis, and then being inserted into said body, the second end being turned inside-out and being sleeved over and secured to the distal end of said body, said folded and closed first end being adapted to remain folded and closed upon the application of pressurized fluid thereto through the catheter body to cause the eversion of said tube from said body and said folded and closed end being adapted at the end of eversion movement of said tube to flip to an inside-out condition and open under continued application of pressurized fluid.

5. A catheter comprising an elongated flexible tubular catheter body, a flexible tube fabricated of non-elastomeric polyethylene having first and second initially open ends, the first end being closed by being folded several times upon itself through a biasing fold to dispose said end normal to the longitudinal axis of said tube, and a plurality of successive lapping folds taken at right angles to said longitudinal axis, and then being inserted into said body, the second end being turned inside-out and being sleeved over and secured to the distal end of said body, said folded and closed first end being adapted to remain folded and closed upon the application of pressurized fluid thereto through the catheter body to cause the eversion of said tube from said body and said folded and closed end being adapted at the end of eversion movement of said tube to flip to an inside-out condition and open under continued application of pressurized fluid.

* * * * *